(12) United States Patent
Reisfeld et al.

(10) Patent No.: US 6,716,406 B2
(45) Date of Patent: Apr. 6, 2004

(54) CONTROL SYSTEM FOR A PHOTOCATALYTIC AIR PURIFIER

(75) Inventors: Bradley Reisfeld, Manlius, NY (US); Robert H. L. Chiang, Manlius, NY (US); Olivier Josserand, La Boisse (FR); Kevin B. Dunshee, Camillus, NY (US); Thierry Jomard, Faramans (FR)

(73) Assignee: Carrier Corporation, Farmington, CT (US)

( * ) Notice: Subject to any disclaimer, the term of this patent is extended or adjusted under 35 U.S.C. 154(b) by 209 days.

(21) Appl. No.: 09/916,875

(22) Filed: Jul. 30, 2001

(65) Prior Publication Data

US 2003/0021720 A1 Jan. 30, 2003

(51) Int. Cl.[7] ............................. B01J 8/00; B01D 51/00
(52) U.S. Cl. ........................ 423/245.1; 55/418; 95/8; 95/12; 96/397; 422/108; 422/110; 422/122; 422/186.3
(58) Field of Search ...................... 422/108, 110, 422/122, 186.3; 423/245.1, 245.3; 55/418; 96/397; 95/8, 12

(56) References Cited

U.S. PATENT DOCUMENTS

| | | | | |
|---|---|---|---|---|
| 5,612,001 A | * | 3/1997 | Matschke | 96/224 |
| 5,835,840 A | * | 11/1998 | Goswami | 422/186.3 |
| 6,368,393 B1 | * | 4/2002 | Hironaka | 96/111 |
| 2002/0094298 A1 | * | 7/2002 | Monagan | 422/5 |

* cited by examiner

Primary Examiner—Stanley S. Silverman
Assistant Examiner—Maribel Medina
(74) Attorney, Agent, or Firm—Wall Marjama & Bilinski LLP

(57) ABSTRACT

In an air conditioning system which includes a catalytic air purifier, a control system is provided for sensing the level of predetermined conditions in a space and for responsively modulating the air purification process in a manner which optimizes the process in terms of its effectiveness and its economical use. The conditions that are sensed include the levels of VOC's, $CO_2$, and biological contaminants, as well as degree of occupancy, relative humidity and air flow. The air purification process is modulated by varying the power to a UV lamp, turning one or more UV lamps on or off, varying the effectiveness of the catalyst, varying the volume or speed of the air flowstream and/or varying the relative humidity in the space.

19 Claims, 6 Drawing Sheets

CONTROL SYSTEM FOR A PHOTOCATALYTIC AIR PURIFIER

BACKGROUND OF THE INVENTION

This invention relates generally to photocatalytic air cleaners and, more particularly, to a control system for modulating the operation thereof.

The process of removing or reducing organic pollutants from a fluid by contacting the fluid with a photoreactive metal semiconductor material in the presence of ultraviolet light has long been known. One application is that of detoxifying the air being conditioned and circulated within a building. That is, within the circulation airstream, an ultraviolet (UV) light is caused to radiate a substrate that is coated with a photocatalyst such as titanium dioxide to thereby bring about a photocatalytic oxidation reaction to eliminate undesirable volatile organic compounds (VOC's) and microbiological contaminants such as bacteria, molds, and viruses that may be in the airstream. Such a process substantially enhances the environmental and health aspects of an air-conditioning system and may even improve the comfort level in the conditioned space.

One approach to operating such a photocatalytic air purifier is to install it into a system in such a way as to have it operating at all times, i.e. with the ultraviolet light being on at all times. While this ensures that the maximum amount of purification will occur, it is also expensive and wasteful since much of that operational time would not be necessary or even effective. For example, during periods in which there is no air flowing over the substrate, such as when the fan is turned off, there would be little or no detoxification occurring and therefore little reason to have the UV lamp on.

Another possibility is that of turning the air purifier on and off with the air-conditioning system. While this will save energy and prolong the life of the UV bulbs, it will still result in the unnecessary use of the air purifier at times when it is not needed and the nonuse of it during periods in which it is needed, such as, for example, when a space has been cooled to a desired temperature but there are still impurities in the air.

It is therefore an object of the present invention to provide a method and apparatus for controlling the operation of a photocatalytic air purifier to obtain effective, efficient and economical use thereof so as to thereby reduce the operational and maintenance costs thereof. This object and other features advantages become more readily apparent upon reference to the following description when taken in conjunction with the appended drawings.

SUMMARY OF THE INVENTION

Briefly, in accordance with one aspect of the invention, a photocatalytic air purifier is controlled so as to operate only to the extent necessary as indicated by conditions within a space. The purification process is therefore optimized with respect to efficiency and economy.

In accordance with another aspect of the invention, the extent of the purifier operation is controlled in response to the sensing of certain conditions in the space. For example, a sensor designed to measure the amount of VOC's or microbiological contaminants is used to control the on/off conditions of the purifier to operate only as necessary to destroy the contaminants that are sensed. When the level of contaminants has been reduced to a predetermined threshold level, the control will automatically shut down the purifier.

By yet another aspect of the invention, the air purification process is controlled not only between the on/off conditions but also by degree of operation. That is, in response to the sensed conditions, the number of UV lamps or the power to the lamps may be selectively varied, for example. Another variable that may be controlled is the "dwell time", which may be varied by controlling the amount of air or the flow of the airstream passing over the air purifier. This can be accomplished by controlling the speed of the fan or the position of the damper.

In the drawings as hereinafter described, a preferred embodiments is depicted; however, various other modifications and constructions can be made thereto without departing from the true spirit and scope of the invention.

DESCRIPTION OF THE PREFERRED EMBODIMENT

Figure 1:
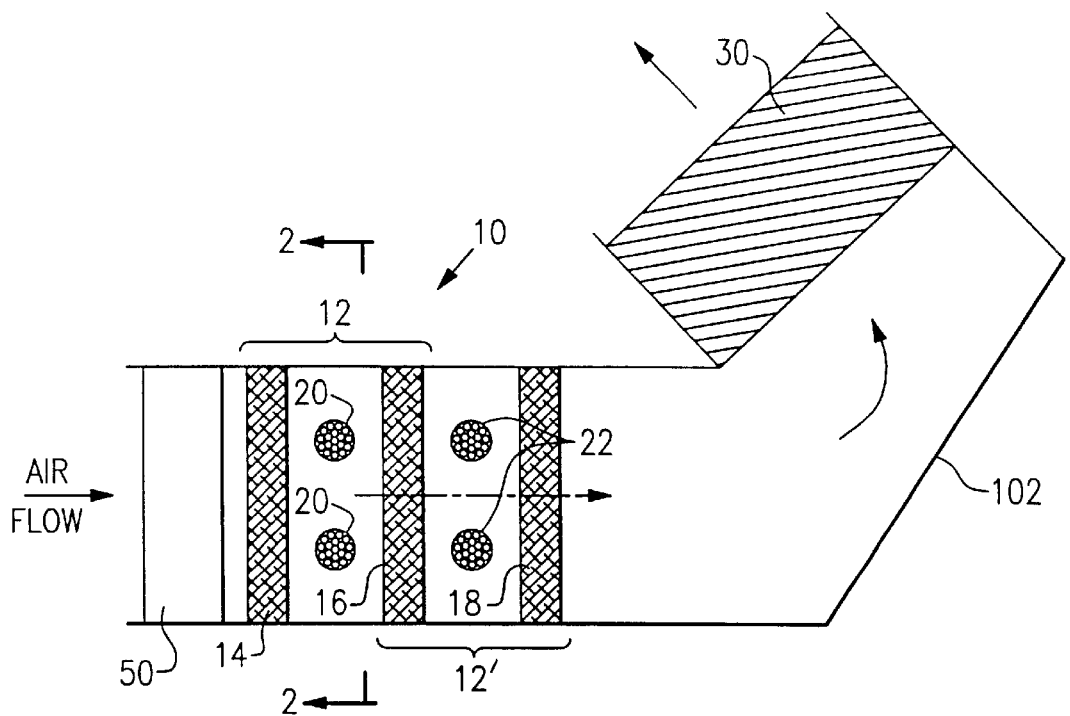
FIG. 1 is a plan view of a photocatalytic purifier in accordance with the present invention.

Reference will now be made in detail to the present preferred embodiments of the invention, examples of which are illustrated in the accompanying drawings. Wherever possible, the same reference numbers will be used throughout the drawings to refer to the same or like parts. An exemplary embodiment of the photocatalytic purifier of the present invention is shown in FIG. 1, and is designated generally throughout by reference numeral 10.

In accordance with the invention, the present invention includes a photocatalytic air purifier for use in a fan coil unit or a duct. The purifier features a modular enclosure having a retractable alignment mechanism. The retractable alignment mechanism is configured to move the enclosure between an in-use position aligned within the fan coil unit and a retracted position. The photocatalytic purifier includes a first honey-combed filter structure having a catalytic layer disposed thereon. A second honey-combed filter structure is disposed adjacent to the first honey-combed filter structure, the second honey-combed filter structure also having the catalytic layer disposed thereon. At least one UV lamp is disposed between the first honey-combed filter structure and the second honey-combed filter structure. The catalytic layer reacts with airborne VOCs and bioaerosols when activated by UV light to thereby oxidize the VOCs and destroy the bioaerosols.

Thus, the photocatalytic purifier of the present invention substantially eliminates odors, VOCs, and bioaerosols from air directed through a fan coil while reducing service and maintenance to a minimum. Further, the photocatalytic air purifier is conveniently installed and removed for maintenance purposes.

As embodied herein and depicted in FIG. 1, a plan view of a photocatalytic purifier in accordance with the present invention is disclosed. Photocatalytic purifier 10 is disposed in fan coil housing 102, between media filter 50 and fan coil unit 30. One of ordinary skill in the art will recognize that this embodiment of the present invention can also be employed in a duct system instead of a fan coil unit. Photocatalytic purifier 10 includes at least one filter layer 12 having at least one UV lamp 20 disposed between honey-combed filter element 14 and honey-combed filter element 16. In the embodiment depicted in FIG. 1, a second photocatalytic purifier layer 12' is formed by disposing UV lamps 22 between filter element 16 and filter element 18. Each additional filter layer 12 increases the efficiency of filter 10. Thus, photocatalytic purifier 10 may include a plurality of filter layers 12 that include at least on UV lamp 20 disposed between honey-combed filter elements 14 and 16. In one embodiment, filter 10 includes stand alone UV lamps disposed proximate to fan coil 30 and the fan coil drip pan (not shown). The purpose of UV lamp is to destroy any microbes that may be attached to fan 30 and its drip pan. In another embodiment, filter 10 does not include UV lamp 24.

Figure 2:
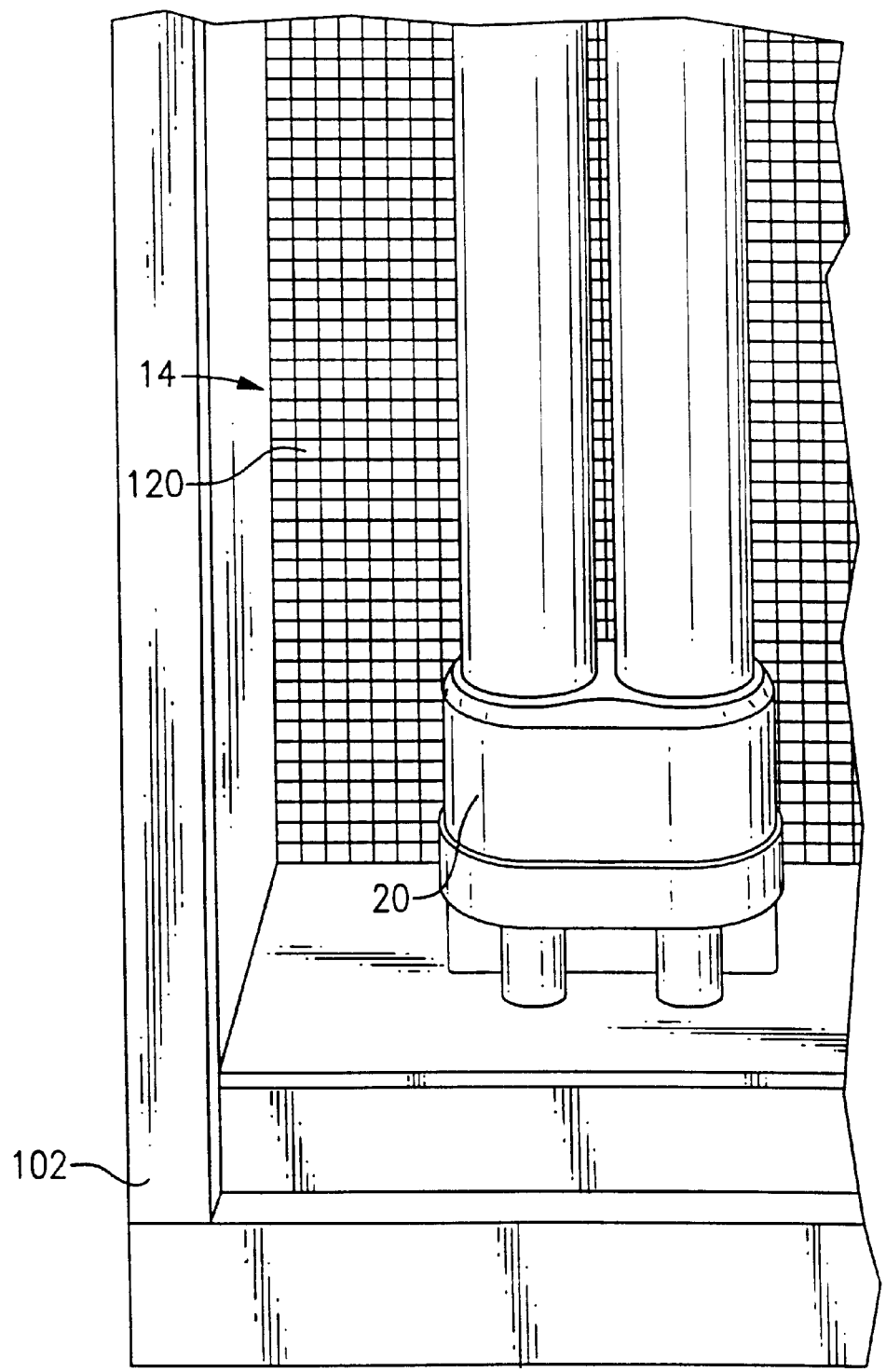
FIG. 2 is a cross-sectional view of the photocatalytic purifier taken through line A—A in FIG. 1.

FIG. 2 is a cross-sectional view of filter 10 taken through line 2—2 in FIG. 1. The cross-sectional view clearly shows the honey-combed structure of filter element 14. Any suitable structure may be employed, however, the honey-combed structure of filter elements 14, 16 and 18 is preferred because air pressure is maintained as air is directed through filter 10. Filter elements 14, 16 and 18 include catalytic coating 120 disposed thereon. As depicted in FIG. 2, UV lamps 20 are positioned to direct UV radiation into the interior of honey-combed filter elements 14 and 16. As shown in FIG. 2, the cross-section of photocatalytic purifier 10 is equal to the cross-section of fan coil housing 102, Thus, purifier 10 purifies the entire volume of air passing through the fan coil.

Figure 3:
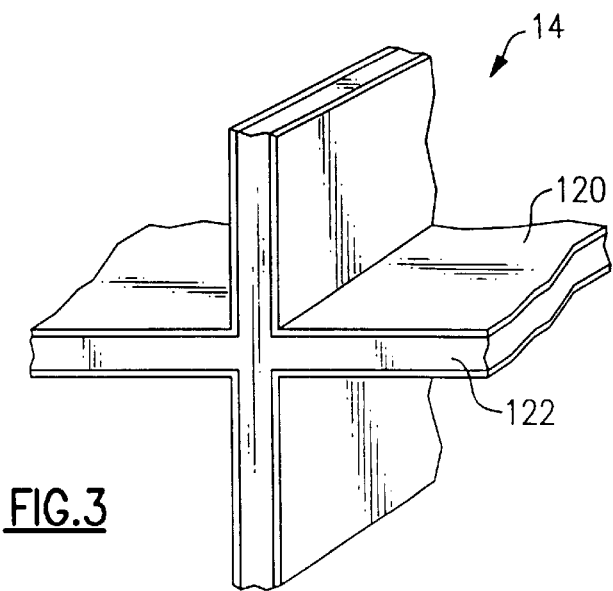
FIG. 3 is a detail view of the honey-combed filter element depicted in FIG. 2.

FIG. 3 is a detail view of honey-combed filter element 14, showing catalytic coating 120 and substrate 122, One of ordinary skill in the art will recognize that any suitable catalytic coating 120 may be disposed on elements 14, 16 or 18, but there is shown by way of example a coating of titanium dioxide. One of ordinary skill in the art will also recognize that nay suitable material may be used as a substrate material for filter elements 14, 16 and 18, but there is shown by way of example a ceramic substrate.

In other embodiments, an aluminum substrate or an FeCrAlY alloy substrate are used. Both the ceramic and aluminum substrates are desirable in applications requiring non-flammable filter elements. If non-flammability is not an issue, substrate 122 used in filter elements 14, 16 and 18 could be fabricated using a paper material. One of ordinary skill in the art will also recognize that any suitable substrate geometry may be used. The geometry can include honey-combs, fins, mesh, a filter-type structure, a fibrous type, or a filamentous structure.

Photocatalytic purifier 10 employs photocatalytic oxidation technology to substantially eliminate odors, VOCs, and bioaerosols. Air propagating through purifier 10 passes over catalytic layer 120. In gas-solid photocatalytic oxidation (PCO), a VOC laden air stream is brought into contact with a titania catalyst disposed on layer 120. The UV light activates the catalyst. The VOCs react with the activated catalyst and are converted into carbon dioxide and water via oxidation. This process occurs at room temperature. Since the process occurs at room temperature, the operating cost is much lower than conventional high temperature thermal oxidizers. PCO destroys a wide range of contaminants in air streams. Filter elements 14, 16, and 18 are not degraded over time by UV light and thus, they do not need to be replaced even after continuous prolonged usage. It should also be mentioned that bioaerosols are also destroyed by their exposure to UV light.

Figure 4:
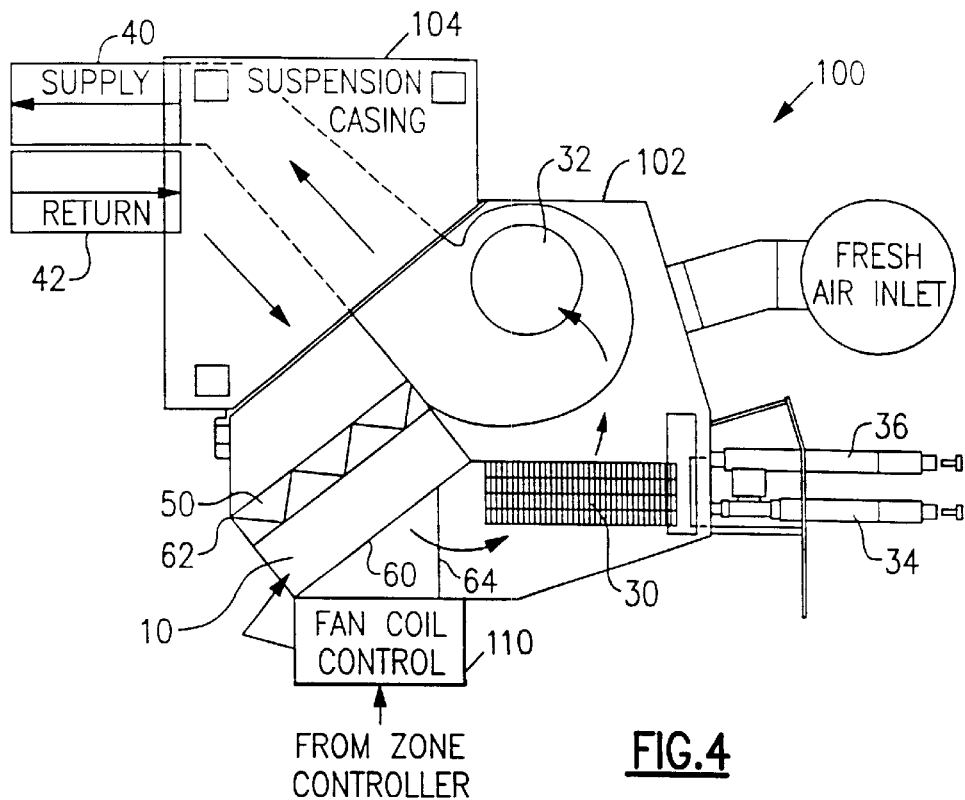
FIG. 4 is a diagrammatic depiction of a fan coil unit in accordance with a first embodiment of the invention showing the photocatalytic purifier depicted in FIGS. 1–3 in an in-use position.
Figure 5:
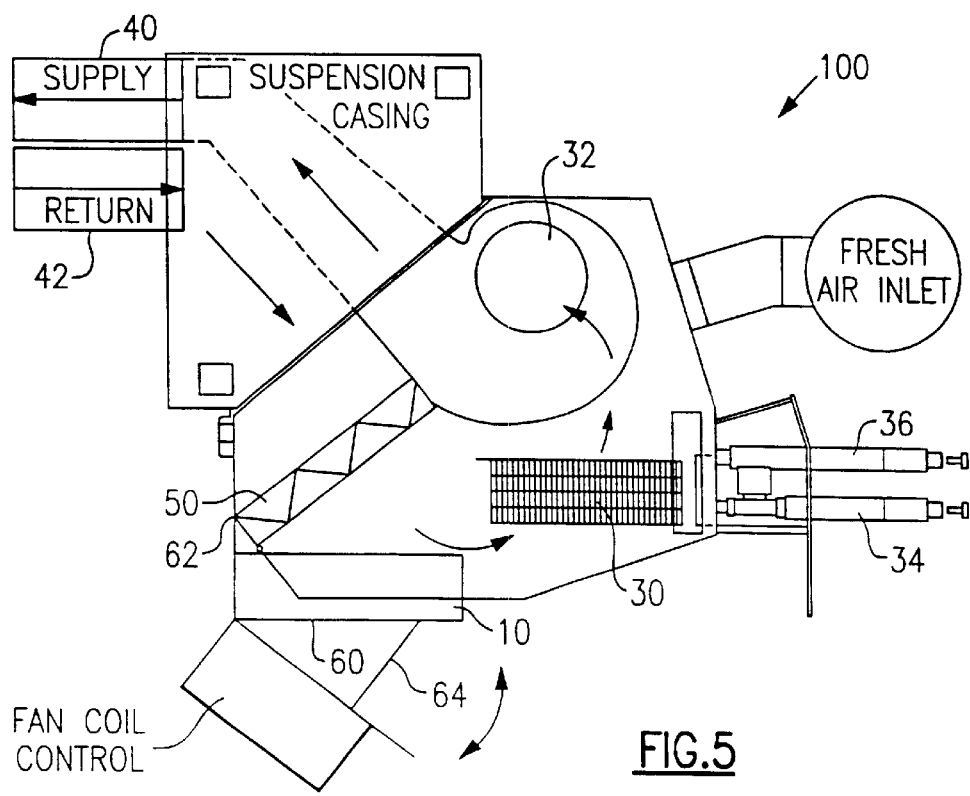
FIG. 5 is a diagrammatic depiction of a fan coil unit in accordance with the first embodiment of the invention showing the photocatalytic purifier depicted in FIGS. 1–3 in a retracted position.

As embodied herein, and depicted in FIG. 4, fan coil unit 100 includes housing 102 which is connected to suspension casing 104. Suspension casing 104 is attached to a ceiling or some other structural element of the building accommodating fan coil unit 100. Fan coil unit 100 includes photocatalytic purifier 10 which is disposed in housing 102 between media filter 50 and fan coil 30. Fan coil 30 includes cold water supply 34 and hot water supply 36. Both cold water supply 34 and hot water supply 36 include valves (not shown) that are controlled by fan coil controller 110 to thereby regulate heating and cooling within the conditioned space. Fan coil unit 100 also includes fan 32 which draws an air stream from air return 42 through photocatalytic purifier 10 and fan coil 30. The air stream is then directed into the conditioned space via air supply duct 40. In FIG. 4, photocatalytic purifier 10 is shown in the in-use position, being disposed adjacent to filter 50. Photocatalytic purifier 10 includes modular enclosure 60 having a retractable alignment mechanism 62. Retractable alignment mechanism 62 is configured to move enclosure 60 between an in-use position aligned within the fan coil unit, and a retracted position. In this embodiment, alignment mechanism 62 is a hinged door structure. Mechanism 62 includes arm 64 that is used to hold enclosure 60 in the in-use position. The retracted position is depicted in FIG. 5.

It will be apparent to those of ordinary skill in the pertinent art that modifications and variations can be made to fan coil control 110 of the present invention depending on cost requirements and the complexity of the application. For example, fan coil unit 100 can be deployed as a stand-alone unit in a single family dwelling, or as one unit among many in a complex architecture. For example, fan coil unit 100 may be employed in a multi-storied structure having a plurality of air-conditioned zones. Fan coil control 110 includes firmware containing the control program necessary to control the water valves, fan 32, and UV lamps 20, 22, and 24 included in photocatalytic purifier 10. The control program is executed by an embedded microprocessor included in fan coil control 110. In another embodiment, fan coil control 110 is implemented using a logic controller.

Fan coil control 110 includes several operational modes. The first mode is an "unoccupied mode." In this mode, the level of comfort provided by fan coil unit 100 does not have to be at an optimum level because no one is in the conditioned space. The heating and cooling of the air conditioned zone is regulated in accordance with a wider "dead-band." Thus, controller 110 allows the ambient air temperature of the air conditioned zone to vary within a wide range temperatures before providing either heating or cooling. The UV lamps are inoperative during this mode.

The second mode is referred to as the "occupied mode." In this mode, the level of comfort provided by fan coil unit 100 is optimized because of the presence of people in the conditioned space. Thus, the UV lamps are always operating in this mode. The occupied mode includes a "demand" sub-mode wherein fan 32 is operating, and a "satisfied" sub-mode wherein fan 32 is inoperative. In other embodiments, controller 110 uses a "tolerance index" as a control metric. Controller 110 may include a motion detector input to determine whether the conditioned space is occupied.

A third mode is provided by controller 110. It is known as the "frost protection mode." The frost protection mode initiates heating within a conditioned space only to maintain a minimum air temperature within the air conditioned space. Since the air conditioned space is assumed to be unoccupied, the UV lamps are not operative in this mode. In addition to temperature sensors, controller 110 may include a sensor input coupled to window contacts, enabling it to recognize an open window condition. In another embodiment, the frost protection mode initiates heating during the open window condition.

As embodied herein and depicted in FIG. 5, a diagrammatic depiction of fan coil unit 100 showing photocatalytic purifier 10 in a retracted position is disclosed. In the retracted position, hinged door structure 62 retracts to provide access to purifier 10 during maintenance or the removal of purifier 10. Arm 64 is detached from purifier 10 during removal.

Figure 6:
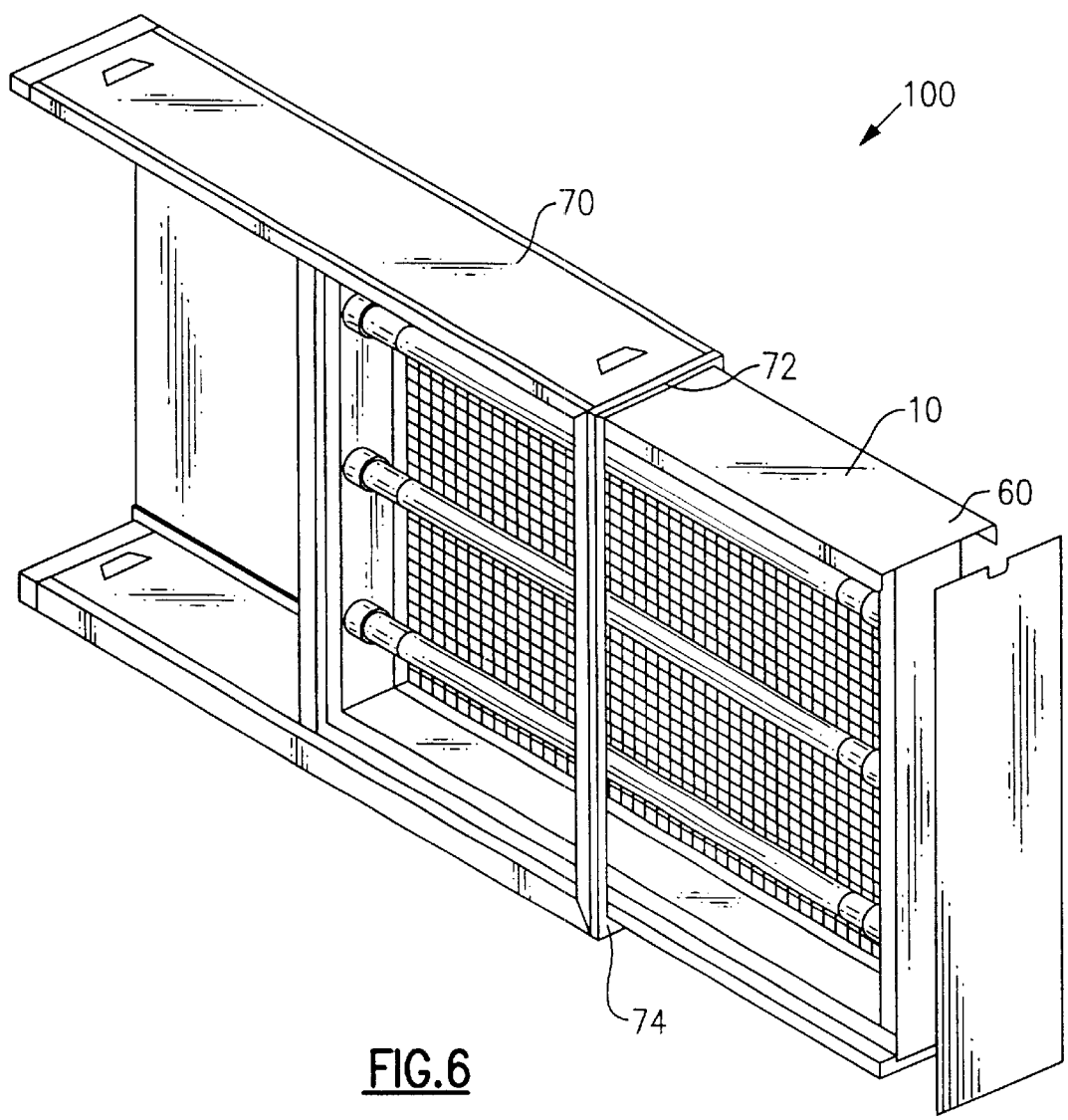
FIG. 6 is a diagrammatic depiction of a fan coil unit in accordance with a second embodiment of the invention showing the photocatalytic purifier depicted in FIGS. 1–3 in a retracted position.

As embodied herein and depicted in FIG. 6, a diagrammatic depiction of photocatalytic purifier unit 100 in accordance with a second embodiment of the invention is disclosed. In this embodiment, unit 100 is disposed in media cabinet 70. The enclosure 60 of photocatalytic purifier 10 is shown in a retracted position. Enclosure 60 is equipped with slider mechanism 72 on a top portion of enclosure 60, and is equipped with slider mechanism 74 on a bottom portion of enclosure 60. One of ordinary skill in the art will recognize that unit 100 can be a fan coil unit or part of a duct system.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

Figure 7:
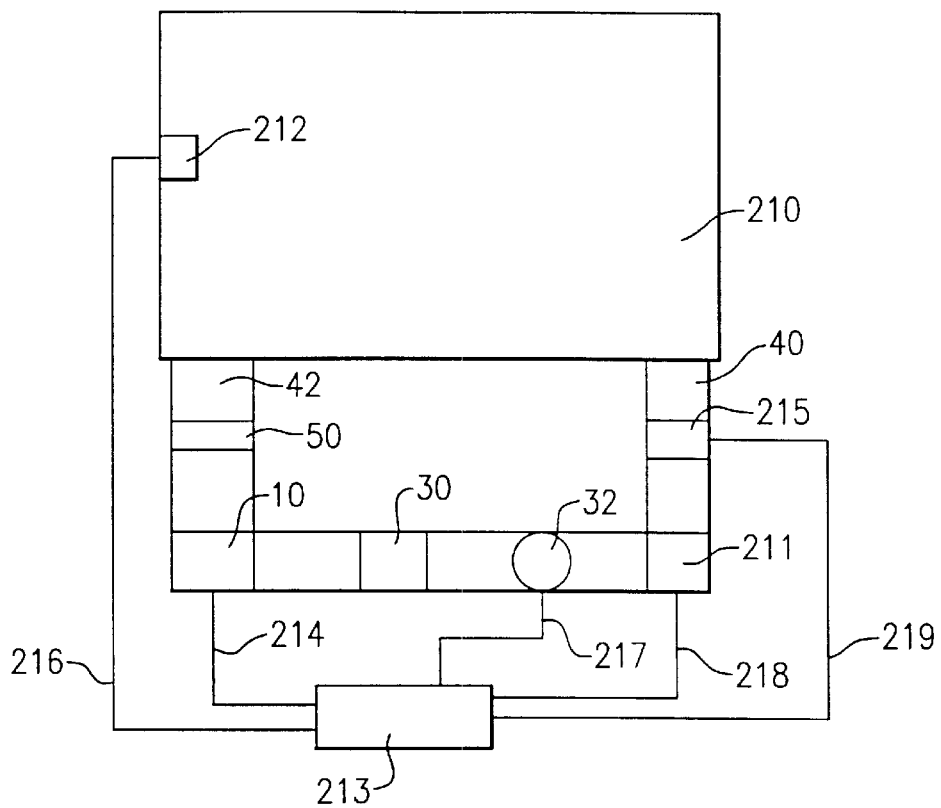
FIG. 7 shows a schematic illustration of the present invention with a control included.

Referring now to FIG. 7, the air purifier 10 is shown as installed in a system between the particle filter 50 and the downstream coil 30. The fan 32 draws air from the conditioned space 210, via the return duct 42 and delivers the conditioned air to the space to 10 by way of the supply duct 40. A damper 211 is provided to selectively regulate the flow speed and volume of air being circulated by the fan 32. A plurality of input devices 212 are provided to sense or otherwise indicate the various conditions within the space 210 for the purpose of purifying the air in a manner to be described hereinafter. The input devices 212 may include sensors that are designed specifically for sensing concentrations of undesirable chemical impurities in the air, such as VOC's, $CO_2$, or biological sensors that are designed to sense the concentrations of particular biological contaminants such as bacteria, molds or viruses. The may also include existing types of sensors that are commonly used in spaces for purposes of adjusting comfort levels, such as temperature, relative humidity, and occupancy sensors. Finally, the diagrammatic block referred to as input devices 212 may also include non-sensor control inputs that are intended to be part of the overall control scheme, such as time based parameters or other inputs that are placed into the system by an operator using a thermostat or by a building management system. For example, they may comprise a day-of-the-week and/or time-of-day indicator which would turn on the air purifier early in the morning on weekdays, operate it to a lesser extent in the afternoons and turn it off at night and on weekends. The sensed conditions, as well as those inputs that are otherwise placed into the system, are applied individually or in combination to modulate the way in which the air purification process is conducted in a manner to be more fully described hereinafter. A humidifier/dehumidifier 215 is provided to introduce or remove water vapor from the air being provided to the space 210.

As will be seen in FIG. 7, a control module 213 is electronically linked to the air purifier 10 by lines 214, to the sensors 212 by lines 216, to the fan 32 by lines 217, to the damper 211 by lines 218 and to the humidifier/dehumidifier 215 by lines 219. Electronic signals will be transmitted from the sensors 212, the air purifier 10, the fan 32 and the damper 211 so that the control module 213 can then transmit control signals to the air purifier 10, the fan 32, and the damper 211 to selectively control their operation in a manner that will bring about a more effective and economical use of the air purification process.

Figure 8:
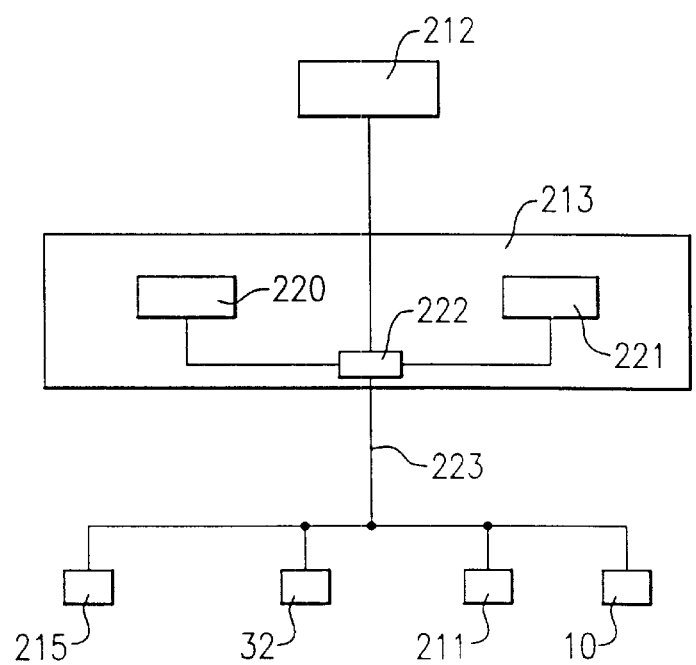
FIG. 8 shows a schematic illustration of the control portion of the present invention.

Referring to FIG. 8, the sensors are represented by a single block 212 but are in actuality a plurality of sensors and other control inputs as described above. For example, a typical VOC sensor that may be used is one commercially available as part number TGS2600 from Figaro Engineering, Inc. A possible $CO_2$ sensor is commercially available from Carrier Corporation as part number 33ZCSENCO2. A typical occupancy detector is commercially available from Leviton Manufacturing Company Inc. as part number 2520W. As for the non-sensor type inputs, a building management system may have a controller which would enter a signal representative of a condition of the building, such as the number of people that would be in the building as determined by the day of the week. Or an operator may enter control information, such as the time that the owner returns home from work, by way of a thermostat or another user interface. Finally, the signals may be feedback signals to indicate the present condition of certain components, such as the speed of the fan 32 or the position of the damper 211.

Within the controller 213 there are certain stored values that represent predetermined threshold parameters or setpoints that are represented by the block 214. For example, a setpoint of 50 ppb for VOC's would indicate that for any level of sensed VOC's below that number, the air purifier 10 would not need to be turned on. If the sensor indicates that the level in the space 210 has reached that threshold level, the air purifier 10 would need to be turned on. Similarly, a typical setpoint for $CO_2$ would be 1000 ppm, and that for mold would be 900 spores/m3.

As an alternative parameter to be applied in the algorithm, the tolerance index may be used. This is the concentration of a chemical divided by its allowable threshold parameter as set forth above. A total tolerance index, which is the summation of all applicable tolerance indices, may also be used. Any tolerance index that is used should, of course, not exceed 1.

Figure 9:
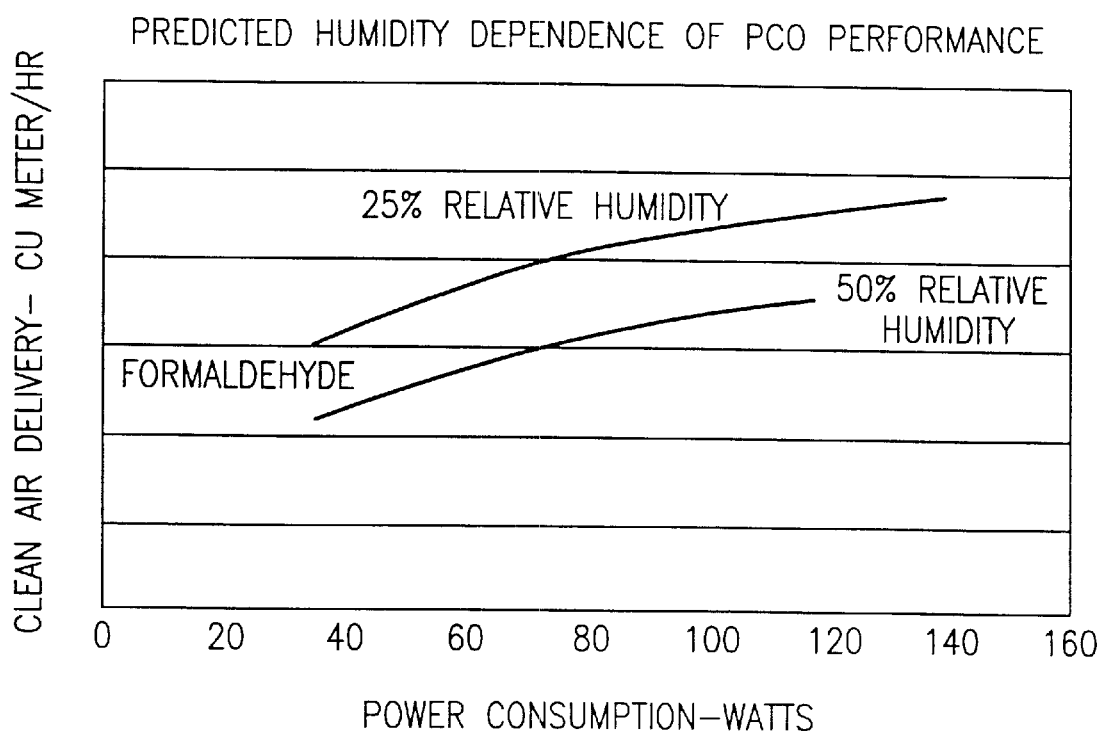
FIG. 9 is a graphical representation of performance of an air purifier as a function of humidity.

In addition to the established setpoints, there are certain empirical data that are installed in the control module 213 as represented by the block 216. That is, based on modeling and experimental studies that relate the performance of air purifiers to environmental parameters (such as air temperature, air flow velocity, and relative humidity), data representative of response characteristics are stored in the control module 213 to be used as part of the control algorithm. For example, FIG. 9 shows a typical plot of clean air delivery rate for the pollutant formaldehyde as a function of lamp power consumption for two different levels of humidity. Similar plots can be made for the dependence of clean air delivery rate on the air temperature (windchill effects) as well as other important effects. Such data can be used in combination with sensed data relating to humidity, temperature, and air flow, for example, to control the system so as to thereby achieve the desired level of clean air delivery, and if used properly may obviate the need for a specific sensor for the pollutant of interest.

Referring again to FIG. 8, a comparator 222 receives signals from the sensors 212, from the setpoint block 220 and from the empirical data block 221 to generate a demand signal 223 that is then applied to the air purifier 10 and/or the fan 32 and/or dehumidifier/dehumidifier to control their operation. For example, based on the sensed needs for air purification, the controller 23 may generate a demand signal 223 that will reduce or increase the amount of power being delivered to the UV lamps or may turn on or off some of the lamps. Similarly, one or more lamps may have their outputs attenuated or increased through some mechanical, electrical, electro-mechanical, magnetic or chemical means. As an alternative, or in addition, the active catalyst surface area in the device may be modulated by the mechanical obscuration of part of the catalyst, for example.

Recognizing that the "dwell time", or the time that the circulated air is exposed to the effect of the air purifier 10, will be dependent on the velocity of the air passing through the air purifier 10, the purification process can also be affected by a modulation of the speed of the fan 32 or the position of the damper 211. For example, a longer dwell time can be accomplished by reducing the speed of the fan 10 or a moving of the damper 211 to a more closed position. If less purification is acceptable, the fan speed may be increased or the damper may be moved to a more fully open position.

Finally, recognizing that the performance of the air purifier 10 is dependent on the humidity of the air passing therethrough, the demand signal 223 can be applied to the humidifier/dehumidifier 215 to cause it to operate in a manner so as to optimize the effectiveness of the air purifier 10 while maintaining a desired comfort level in the space 210.

While the present invention has been particularly shown in described with reference to a preferred embodiment as illustrated in the drawings, it will be understood by one skilled in the art that various changes in detail may be affected therein without departing from the spirit and scope of the invention as defined by the claims.

What is claimed:

1. A control for an air treatment system of the type having a return air duct, a supply air duct, a fan for causing air to be circulated through the system, and an air purifier within the system having at least one catalytic coated substrate with which the circulated air comes into contact, and at least one UV lamp disposed near the substrate for illumination thereof for oxidizing organic compounds in the circulated air, comprising:
    an input device for indicating a condition in a conditioned space and generating a demand signal representative thereof;
    modulation means for modulating between various degrees, the operation of said air purifier in response to said demand signal said modulation means being operated to vary the power to said at least one UV lamp.

2. A control as set forth in claim 1 wherein said modulation means is operative to turn at least one UV lamp on or off.

3. A control as set forth in claim 1 wherein said modulation means is operative to modulate the degree to which the catalytic coated substrate is exposed to said UV lamp.

4. A control as set forth in claim 1 wherein said modulation means is operative to modulate the speed of said fan.

5. A control as set forth in claim 1 wherein said modulation means is operative to modulate the position of a damper within said supply air duct.

6. A control as set forth in claim 1 wherein said input device includes a sensor for sensing a condition in a space and generating a signal representative thereof.

7. A control as set forth in claim 6 and including comparing means for comparing said sensed condition signal with a threshold signal representative of a desired condition in said space and generating said demand signal in response to the difference thereof.

8. A control as set forth in claim 6 wherein said sensor is a VOC sensor which is operative to sense levels of volatile organic compounds in said conditioned space.

9. A control as set forth in claim 6 wherein said sensor is a biological contaminants sensor which is operative to sense levels of biological contaminants in said conditioned space.

10. A control as set forth in claim 6 wherein said sensor is an occupancy sensor which is operative to sense the degree of occupancy of said conditioned space.

11. A control as set forth in claim 1 and including a memory for storing selected parameters representative of desired conditions in said conditioned space and means for generating threshold signals representative thereof.

12. A method of controlling an air treatment process in an air conditioning system of the type having a fan for circulating air to a space to be conditioned and a photocatalytic air purifier disposed in a flowstream of said air for purifying said air, comprising the steps of:
    sensing a condition of said space and generating a signal representative thereof;
    comparing said sensed condition signal with a predetermined threshold level and generating a demand signal in response thereto; and
    modulating between various degrees, the operation of said air purifier in response to said demand signal by varying the power to a UV lamp.

13. A method as set forth in claim 12 wherein said step of modulating is that of turning a UV lamp on or off.

14. A method as set forth in claim 12 wherein said step of modulating is that of varying the degree to which the catalytic coated substrate is exposed to said UV lamp.

15. A method as set forth in claim 12 wherein said step of modulating is that of modulating the speed of said fan.

16. A method as set forth in claim 12 wherein said step of modulating is that a varying the position of a damper within said flowstream.

17. A method as set forth in claim 12 wherein the condition sensed is that of the level of volatile organic compounds in said conditioned space.

18. A method as set forth in claim 12 wherein the condition sensed is that of the level of biological contaminants in said conditioned space.

19. A method as set forth in claim 12 wherein the condition sensed is that of the degree of occupancy of said conditioned space.

* * * * *